United States Patent [19]

Tann et al.

[11] Patent Number: 4,831,123

[45] Date of Patent: May 16, 1989

[54] PROCESS FOR PREPARING NETILMICIN

[75] Inventors: Chou-Hong Tann, Berkley Heights; Tiruvettipuram K. Thiruvengadam, Woodbridge; John S. Chiu, Parsippany; Cesar Colon, Roselle Park, all of N.J.

[73] Assignee: Schering Corporation, Kenilworth, N.J.

[21] Appl. No.: 927,765

[22] Filed: Nov. 6, 1986

Related U.S. Application Data

[63] Continuation-in-part of Ser. No. 787,193, Oct. 15, 1985, abandoned.

[51] Int. Cl.$^4$ .................... A61K 31/71; C07H 15/22; C07D 7/04
[52] U.S. Cl. .................... 536/13.9; 536/13.6; 536/13.7; 536/16.8; 536/18.5
[58] Field of Search .................... 536/13.6, 13.7, 13.9, 536/16.8, 18.5

[56] References Cited

U.S. PATENT DOCUMENTS

| | | | |
|---|---|---|---|
| 4,002,742 | 1/1977 | Wright et al. | 536/16.8 |
| 4,020,269 | 4/1977 | Hiraga et al. | 536/16.8 |
| 4,024,332 | 5/1977 | Fenner et al. | 536/13.6 |
| 4,294,959 | 10/1981 | Voss et al. | 536/13.9 |
| 4,335,114 | 6/1982 | Voss et al. | 536/13.9 |
| 4,347,354 | 8/1982 | Cron et al. | 536/13.7 |
| 4,380,625 | 4/1983 | Stadler et al. | 536/13.6 |

FOREIGN PATENT DOCUMENTS

| | | | |
|---|---|---|---|
| 2840907 | 4/1980 | Fed. Rep. of Germany | 536/13.9 |
| 1033394 | 6/1966 | United Kingdom | 536/13.7 |

OTHER PUBLICATIONS

Nagabhushan et al.; Carbohydrate Research, 130:243–249, (1984).

Primary Examiner—Ronald W. Griffin
Assistant Examiner—Nancy S. Carson
Attorney, Agent, or Firm—John J. Maitner; Stephen I. Miller; James R. Nelson

[57] ABSTRACT

A high yielding process for converting 3,2',6'-tri-N-acetyl sisomicin to netilmicin comprising the step of silylating the starting material at the 5,2' positions, and optionally at the 4' position, converting the 1-amino substituent to a 1-N-imino substituent, converting the imino to an ethylamino, deprotecting the compound and recovering netilmicin. Also disclosed are novel intermediate compounds.

31 Claims, No Drawings

PROCESS FOR PREPARING NETILMICIN

CROSS REFERENCE TO RELATED APPLICATIONS

This application is a continuation-in-part of application Ser. No. 787,193 filed Oct. 15, 1985, now abandoned.

BACKGROUND

This invention relates to an improved process for converting sisomicin to netilmicin (1-N ethylsisomicin).

More particularly, this invention relates to a process for converting selectively blocked sisomicin to a 1-N-imine derivative, then reducing the imine to a 1-N-ethyl derivative (netilmicin) under conditions which result in high yields of the desired compound with very low yields of interfering co-products.

Netilmicin, which has the formula

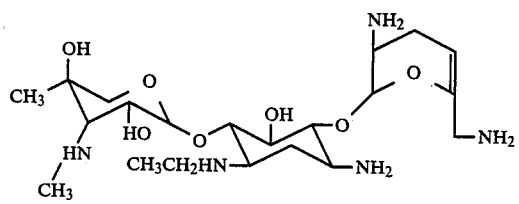

is a well known aminoglycoside antibiotic. The antibiotic and its preparation are described in U.S. Pat. Nos. 4,002,742; 4,029,882; 4,230,847 and 4,337,335. Originally netilmicin was prepared by reacting sisomicin sulfate with acetaldehyde under reducing conditions. Since, however, sisomicin has five amino groups, this procedure led to an unusually high percentage of undesired products and the overall yield was only about 10–11%. The process described in U.S. Pat. Nos. 4,230,847 marked a substantial improvement. By using copper complexes, selective blocking of the 3,2' and 6' amino groups of sisomicin was obtained.

Alkylation by means of acetaldehyde in the presence of a reducing agent of this intermediate led to substantial improvement in yield (60% yield in the laboratory, 49% in commercial manufacture).

However, this improved process also results in formation of a substantial percentage of undesired products which reduces the overall yield. The largest quantity of undesired side-product consists of 1,1-N-diethyl-sisomicin. Under the conditions used in the process referred to above, i.e., reaction with acetaldehyde in the presence of a reducing agent, unreacted or excess acetaldehyde seems to react with already formed 1-N-ethylated sisomicin to form the 1,1-diethylated product.

This invention relates to an improvement of the above process resulting in less side reactions and, accordingly, higher yields. The process of this invention comprises:

(a) reacting acetaldehyde in an inert aprotic solvent under anhydrous conditions with a selectively blocked sisomicin derivative of the general formula

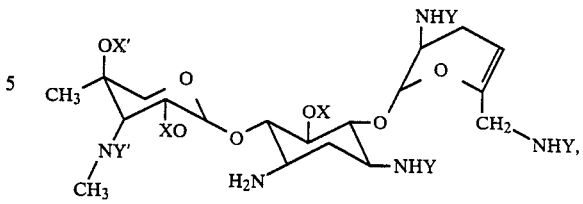

wherein each X is an organosilyl group

with $R^1$ to $R^3$ independently being lower alkyl, phenyl or phenyllower alkyl; $X'$ is hydrogen or an organosilyl group as defined above; each Y represents an amino blocking group, and $Y'$ represents hydrogen or an amino blocking group, to form the corresponding 1-N-ethylidene derivative;

(b) reducing any excess of unreacted acetaldehyde present in the reactive mixture, preferably under anhydrous conditions;

(c) reducing the 1-N-ethylidene group to the ethylamino group under aqueous or anhydrous conditions;

(d) removing all protecting groups; and (e) isolating the netilmicin in free base form or in the form of an acid addition salt.

The sisomicin derivative is reacted with amino-blocking compounds at the 3,2',6' and optionally at the 3'' position. Preferred amino-blocking substituents comprise acetyl, formyl, propionyl and aroyl groups, with acetyl substituents being particularly preferred. The methods by which the acetyl, propionyl and aroyl groups are added to the sisomicin are disclosed in U.S. Pat. No. 4,337,335, the disclosure of which is incorporated herein by reference. The formyl substituent could be added by reaction of sisomicin with unsymmetric formic anhydride.

The formation of 3,2',6'-tri-N-acetyl sisomicin (hereinafter Compound 1) from sisomicin also is disclosed in U.S. Pat. Nos. 4,230,848 and 4,136,254. Example 16C (1) of each patent shows the reaction of cupric acetate hydrate with sisomicin followed by reaction with acetic anhydride and then hydrogen sulfide gas. The product is recovered from an ion exchange resin in the hydroxide cycle. The specific example is incorporated herein by reference.

Another method of manufacturing 3,2',6'-tri-N-acetyl sisomicin from sisomicin is as follows. To cupric acetate suspended in an approximate 6:2 mixture of N,N-dimethylformamide and water, sisomicin concentrate is added. By the addition of triethylamine, the pH is adjusted to 8.5–10.5. The suspension is cooled to about 5° C., and a solution of acetic anhydride in N,N-dimethylformamide is gradually added at 0°–10° C. with efficient agitation. The pH of the reaction mixture is maintained at 8.5–10.5 by adding more triethylamine, as required. Alternatively, about 90% of the acetic anhydride solution in N,N-dimethylformamide, is added first as described. The remaining 10% of the solution is diluted with ca. 6 volumes of N,N-dimethylformamide, and added subsequently. The reaction is monitored for completion by thin-layer chromatography. If not complete, increments of acetic anhydride solution in N,N-dimethylformamide may be added, to complete the reaction. After the reaction is complete, the mixture is concentrated, under reduced pressure. The concentrate is diluted with water, cooled for about four hours at 0° to 10° C., and filtered to remove the solids. The product again is recovered from an ion exchange resin in the partial ammonium cycle.

The 3,2',6'-tri-N-acetyl sisomicin produced by either process then is spray dried to remove the water.

By means of the process of this invention yields of about 85% to 90% or more of netilmicin based on the starting material (Compound 1) are obtained with about 3% to 7% unreacted sisomicin, generally about 5%, and negligible side reaction products.

In the first step of the process of this invention 3,2',6'-tri-N-acetylsisomicin (compound 1) is silylated. In addition to blocking potential reaction sites, silylation also improves the solubility of the sisomicin derivative in the solvent. The silylation agents comprise organosilyl compounds which react with the hydroxyl sites resulting in organosilyl substituents of the general formula

with $R^1$ to $R^3$ being lower alkyl, phenyl or phenylloweralkyl. Preferred substituents are triloweralkylsilyls, with trimethylsilyl substituents being particularly preferred.

The three hydroxyl sites, i.e., the 5,2" and 4" may be silylated. However, it also is within the scope of the invention that only two sites may be silylated, i.e., the 5 and 2" sites. This may be accomplished by the proper selection of silylating agent, silylation conditions, and regulation of the quantity of silylation agent added. The extent to which the sisomicin derivative has been silylated could be monitored by NMR. To simplify the silylation process and to improve the solubility, it is preferred to silylate all three hydroxyl sites. In the preferred process depicted below 3,2',6'-tri-N-acetysisomicin is silylated to 3,2',6'-tri-N-acetyl-5,2",4"-trimethyl silul sisomicin (compound 2) according to the following reaction scheme.

SCHEME A

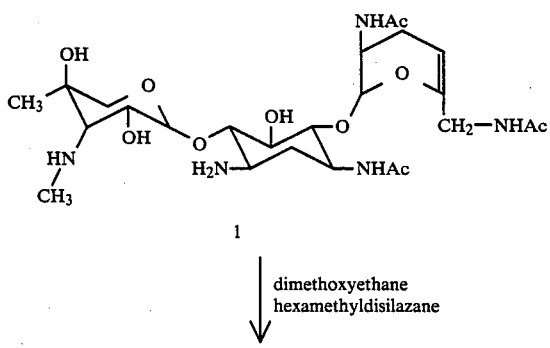

1

| dimethoxyethane
| hexamethyldisilazane
↓

-continued
SCHEME A

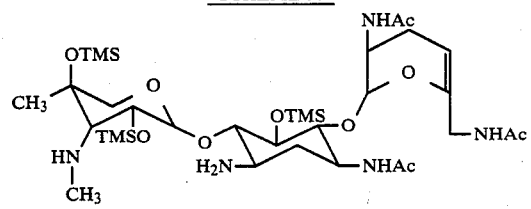

The reaction depicted in Scheme A is conducted under anhydrous conditions at reflux, preferably in the presence of a catalyst, such as a sulfate salt; an ammonium salt, such as ammonium chloride or ammonium sulfate; sulfuric acid; or trimethylsilyl chloride. A preferred catalyst is the sulfate salt of compound 1, i.e., 3,2',6'-tri-N-acetylsisomicin sulfate. The reaction of compound 1 (mixed with a very minor amount of its sulfate salt) and a silylating agent, e.g. a trimethyl silylating agent such as hexamethyldisilazane, bis(trimethylsilyl) acetamide (BSa), mono(trimethylsilyl) acetamide (MSa), trimethylchlorosilane (TMCs) or other equivalent silylating agent is carried out in an inert organic solvent i.e. an organic solvent which is inert to the reaction conditions, e.g. acetonitrile, toluene, 1,2-dimethoxyethane and the like. A preferred solvent is 1,2-dimethoxyethane (DME). The progress of silylation is monitored by 'H-NMR. The reaction is completed in about 5 hours. The silylated substituent is used to block alkylation at the 3"-amine group because of steric hindrance at the trimethylsilylated 2"- and optionally at the 4"-positions.

The 1-amino group of compound 2 is then converted to an N-imino according to the following reaction scheme under preferably anhydrous conditions. The presence of water during the N-imino formation step may result in incomplete reactions at the 1 position.

SCHEME B

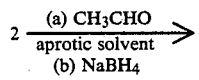

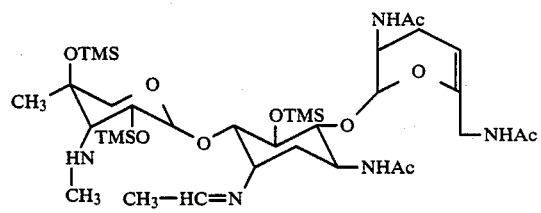

3

This imine formation reaction is the key reaction in the multistep process of this invention. The reaction of compound 2 with acetaldehyde is carried out at temperatures between about 10° C. and room temperature (about 25° C.), preferably at about 15° C., in an organic aprotic solvent which is inert to the reaction conditions, e.g. 1,2-dimethoxyethane, acetonitrile, toluene, hexane, methylene chloride, tetrahydrofuran and the like. A preferred solvent is methylene chloride. After the reaction proceeds for about 30 minutes, a metal hydride reducing agent is added to the mixture, preferably still maintained under anhydrous conditions, to completely react any excess acetaldehyde and thus prevent any undesired side reactions. Preferred reducing agents comprise sodium borohydride, amine boranes, lithium aluminum hydride, with sodium borohydride being particularly preferred. The sodium borohydride, is added and the reaction mixture is warmed to about room temperature and reacted for about 10 to 15 minutes. The imine formation is monitored by 'H-NMR. The first step of the reaction is completed in about 30 minutes. The sodium borohydride reduces any unreacted acetaldehyde, thus preventing undesired side reactions.

After the excess acetaldehyde has been eliminated the amino substituent may be reduced to the ethylamino functionality by a reducing agent, such as those previously described, under aqueous or anhydrous conditions. A buffering agent preferably is added and the pH maintained in the range of about 7-12, preferably about 9.5-10. When sodium borohydride is used as the reducing agent for this step, a protonating agent, such as water and/or a buffering agent, preferably is present. This reaction is set forth below as Scheme C.

SCHEME C

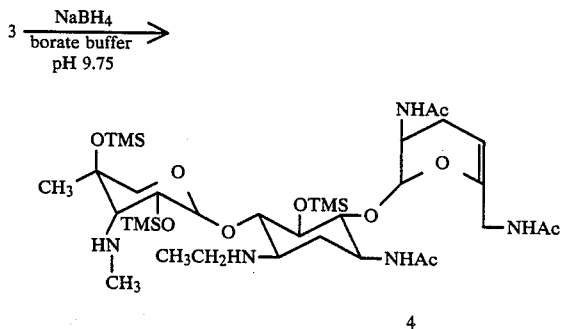

Any conventional buffer which will maintain the pH at about 7-12 is suitable, as for example, phosphate, citrate or borate buffers. Borate buffers are preferred. The buffer is quickly added to the reaction mixture which is then stirred at ambient temperatures for about 15 to 120 minutes until the reaction of reducing the imine is complete. The progress of the reaction can be monitored by 'H-NMR.

The acetyl and trimethyl silyl groups are removed from compound 4 by hydrolysis to obtain netilmicin, compound 5, as illustrated in the following reaction scheme.

SCHEME D

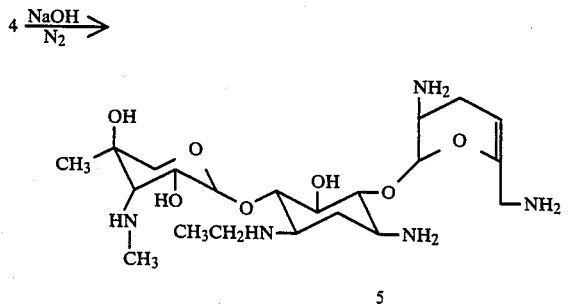

Prior to deblocking compound 4 by hydrolysis, sufficient sodium hydroxide is added initially to deactivate the sodium borohydride and then the solvent is removed from the reaction mixture. This should be done as soon as the reaction is completed. The deblocking by hydrolysis is a conventional procedure. It has been found that when a base, preferably 10% sodium hydroxide, is then added and the hydrolysis reaction is conducted at reflux under nitrogen for about 10-20 hours, a satisfactory result is obtained. The progress of the reaction can be monitored by thin layer chromatography. The resulting hydrolysate is acidified to pH 6 and netilmicin is recovered in a yield of about 85 to 90%.

The following processes illustrate the invention. In the examples HPLC means High Performance Liquid Chromatography, NMR means Nuclear Magnetic Resonance.

EXAMPLE 1

Tri-Silylated Tri-N-Acetyl Sisomicin (a) Charge 15.0 g (26.2 mmoles; 83% purity by HPLC) 3,2',6'-tri-N-acetylsisomicin, 0.750 g (1.12 mmoles) 3,2',6'-tri-N-acetylsisomicin sulfate, 150 ml 1,2-dimethoxyethane (DME) and 25 ml hexamethyldisilazane (118.5 mmoles) to a 500 ml 3-neck round bottom flask equipped with an overhead mechanical stirring device, a reflux condenser stoppered with a drying tube, and a thermometer. Heat the mixture to reflux in an oil bath (external oil bath temp. at 105° C.) for 5 hours, and monitor the progress of silylation by 'H-NMR. The silylation reaction is complete at the 5,2" and 4" sites in about 3-8 hours.

Silylated 1-N-ethyl 3,2',6'-Tri-N-Acetyl Sisomicin (b) Add 150 ml methylene chloride to the anhydrous reaction mixture from part (a) at room temperature. Cool the mixture to about 15° C. before adding 3.0 ml cold acetaldehyde (53.6 mmoles) into it. Continue stirring for 30 min., and then add 1.9 g powdered sodium borohydride (50.2 mmoles). Warm the reaction mixture back to room temperature, and allow it to stir for 10 to 15 min to completely eliminate any excess acetaldehyde. Then, add 30 ml 0.5M aqueous borate buffer (pH 9.75) at a fast drop rate from an additional funnel into the mixture, and allow it to stir at ambient temperature for 2 hours to reduce the imine to the corresponding ethylamino substituent.

Netilmicin

Add 30 ml of 10% aqueous sodium hydroxide solution to the reaction mixture from part (b) to deactivate sodium borohydride. The solvent mixture, DME/CH$_2$Cl$_2$, is removed under reduced pressure. Then charge 200 ml 10% aqueous sodium hydroxide solution, and heat the mixture to reflux in an oil bath (103° C.) under a gentle stream of nitrogen gas for 20 hours. Monitor the progress by thin layer chromatography (TLC) using the lower phase of 1:1:1-chloroform:methanol:concentrated ammonium hydroxide as developing solvent.

Cool the hydrolysate with an ice bath, acidify it to pH6 using 25% aqueous sulfuric acid, and filter off the precipitate. Dilute an aliquot of the filtrate to an appropriate concentration of HPLC assay. A corrected HPLC yield for netilmicin is 88%.

EXAMPLE II

Preparation of 2'',5-disilyl-3,2',6'-Tri-N-Acetyl Sisomicin

To a stirred suspension of 4.0 g (6.04 mmol, 86.6% purity by HPLC) 3,2',6'-tri-N-acetyl sisomicin and 0.04 g (0.06 mmol) 3,2',6'-tri-N-acetyl sisomicin sulfate, in 40 ml 1,2-dimethoxy ethane (DME) was added 4.4 ml hexamethhyldisilazane and the mixture was heated to reflux in an oil-bath for 3 hours. The reaction mixture turned into a clear homogeneous solution and was stopped at this stage ('H-NMR showed that the mixture contained major amounts of 2'',5-disilylated tri-N-acetyl sisomicin).

The imine formation, reduction and hydrolysis was carried out as described in Example I.

A corrected HPLC yield for netilmicin is 83%.

EXAMPLE III

Preparation of Netilmicin from 3,2',6',3''-Tetra-N-Acetylsisomicin

The purified 3,2',6',3''-tetra-N-acetylsisomicin used for this study was obtained by acetylating the 3'' amino group of 3,2',6'-tri-N-acetylsisomicin with N-acetylimidazole and isolating by silica gel column.

4 g of this lyophilized tetra-N-acetyl sisomicin was suspended in 40 ml of DME and 4.4 ml of HMDS was added. The mixture was heated to reflux for 7 hours. 'H-NMR showed that the silylation reaction was complete.

Imine formation, reduction, and hydrolysis was carried out in a similar manner to that described in Example I. A corrected HPLC yield for netilmicin is 83.5%.

The 'H-NMR of 3,2',6'-tri-N-acetyl-5,2'',4'' trimethylsisomicin and 3,2',6', tri-N-acetyl 5,2'',4'' 1-N-ethylidene sisomicin are set forth in Table I below.

TABLE I

A. Tri-silylated tri-N—acetylsisomicin:

'HNMR (CD$_2$Cl$_2$) δ = 0.118 [S, 9H, Si—(CH$_3$)$_3$], 0.124 [S, 9H Si—(CH$_3$)$_3$], 0.165 [S, 9H, Si—(CH$_3$)$_3$], 1.38

(S, 3H, CH$_3$ at C-4'') 1.93 (S, 3H, CH$_3$—C—N), 1.96 (S, 3H,
$\phantom{xxxxxxxxxxxxxxxxxxxxxxxxxxx}\|$
$\phantom{xxxxxxxxxxxxxxxxxxxxxxxxxxx}$O CH$_3$C—N), 1.98 (S, 3H, CH$_3$—C—N), 2.45 (S, 3H, CH$_3$—N
$\|\phantom{xxxxxxxxxxxxxxxxx}\|$
O$\phantom{xxxxxxxxxxxxxxxx}$O at C-3''), 4.69 (dd, 1H, J = 3.29 and 4.02 Hz, CH at C-4'), 5.01 (d, 1H, J = 2.19 Hz, CH at C-1''), 5.08 (d, 1H, J =

1.82 Hz, CH at C-1'), 6.03 (d, 1H, J = 6.99 Hz, NH—C—),
$\phantom{xxxxxxxxxxxxxxxxxxxxxxxxxxxxxxxxxxxxxxxxxxxxxxxx}\|$
$\phantom{xxxxxxxxxxxxxxxxxxxxxxxxxxxxxxxxxxxxxxxxxxxxxxxx}$O 6.47 (dd, 1H, J = 5.11 and 6.96 Hz, CH$_2$NH—C—), and
$\phantom{xxxxxxxxxxxxxxxxxxxxxxxxxxxxxxxxxxxxxxxxxxxxx}\|$
$\phantom{xxxxxxxxxxxxxxxxxxxxxxxxxxxxxxxxxxxxxxxxxxxxx}$O 7.1 ppm (d, 1H, J = 9.13 Hz, NH—C—).
$\phantom{xxxxxxxxxxxxxxxxxxxxxxxxxxxxxxxxx}\|$
$\phantom{xxxxxxxxxxxxxxxxxxxxxxxxxxxxxxxxx}$O B. Silylated 1-N—ethylidene 3,2'-6'-tri-N—acetylsisomicin:

'HNMR (CD$_3$CN) δ = 0.08 [S, 9H, Si—(CH$_3$)$_3$], 0.102 (S, 9H, Si—(CH$_3$)$_3$], 0.140 [S, 9H, Si—(CH$_3$)$_3$], 1.5

(S, 3H, CH$_3$ at C-4''), 1.83 (S, 3H, CH$_3$C—N), 1.86 (S, 3H,
$\phantom{xxxxxxxxxxxxxxxxxxxxxxxxxxxxxxxxxxxxxx}\|$
$\phantom{xxxxxxxxxxxxxxxxxxxxxxxxxxxxxxxxxxxxxx}$O

TABLE I-continued

CH$_3$C—N), 1.89 (d, J = 4.76 Hz, CH$_3$CH=N), 1.93 (S,
$\|$
O

3H, CH$_3$CN), 2.36 (S, 3H, CH$_3$—N at C-3''), 4.71 (bm, 2H,
$\phantom{xxxxxxxxxxxxxxxxxxxxxxxxxxx}\|$
$\phantom{xxxxxxxxxxxxxxxxxxxxxxxxxxx}$O CH's at C-4' and C-1''), 5.19 (d, 1H, J = 1.46 Hz, CH at C-1') 6.37 (d, 1H, J = 8.04, NH—C), 6.77 (d, 1H, J = 8.4
$\phantom{xxxxxxxxxxxxxxxxxxxxxxxxxxxxxxxxxxxxxxx}\|$
$\phantom{xxxxxxxxxxxxxxxxxxxxxxxxxxxxxxxxxxxxxxx}$O Hz, NH—C—), 6.99 (t, 1H, J = 5.48 Hz, CH$_2$—N—C—)
$\phantom{xxxxxxxxxxx}\|\phantom{xxxxxxxxxxxxxxxxxxxxxxxxxxxxxxxxxxxxx}|\phantom{x}\|$
$\phantom{xxxxxxxxxxx}$O$\phantom{xxxxxxxxxxxxxxxxxxxxxxxxxxxxxxxxxxxxxxxxx}$H O and 7.69 ppm (q, 1H, J = 4.76 Hz CH$_3$CH=N), CNMR (CD$_3$CN) δ = 162.04 (N=CHCH$_3$) and 22.46 ppm (N=CH—CH$_3$).

We claim:

1. A process for preparation of netilmicin by 1-N-ethylation of sisomicin by means of acetaldehyde, which comprises
    (a) reacting acetaldehyde in an inert aprotic solvent under anhydrous conditions with a selectively blocked sisomicin derivative of the formula

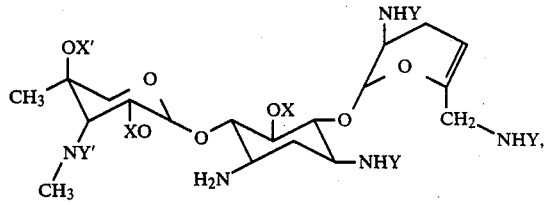

wherein each X is an organosilyl group

with R$^1$ to R$^3$ independently being lower alkyl, phenyl or phenyllower alkyl; X' is hydrogen or an organosilyl group as defined above; each Y represents an amino blocking group; and Y' represents hydrogen or an amino blocking group, to form the corresponding 1-N-ethylidene derivative;
    (b) reducing any excess of unreacted acetaldehyde present in the reaction mixture with a metal hydride reducing agent;
    (c) reducing the 1-N-ethylidene group to the ethylamino group under aqueous conditions with a metal hydride reducing agent by adjusting the pH of the reaction mxture to pH 7–12;
    (d) removing all protecting groups by basic hydrolysis; and
    (e) isolating netilmicin in free base form or in the form of an acid addition salt.

2. The process of claim 1 wherein the excess or unreacted acetaldehyde present in the reactive mixture is reduced under anhydrous conditions.

3. The process of claim 1 wherein the amino protecting group is selected from the group consisting of acetyl, formyl, propionyl, aroyl and mixtures thereof.

4. The process of claim 3 wherein the amino protecting group is acetyl.

5. The process of claim 4 wherein X' is an organosilyl group.

6. The process of claim 5 wherein $R^1$, $R^2$ and $R^3$ are lower alkyl.

7. The process of claim 6 wherein $R^1$, $R^2$ and $R^3$ are each methyl.

8. The process of claim 1 wherein the aprotic solvent is selected from the group consisting of 1,2 dimethoxyethane, acetonitrile, toluene, hexane, methylene chloride, tetrahydrofuran and mixtures thereof.

9. The process of claim 8 wherein the aprotic solvent is dimethoxyethane.

10. The process of claim 2 wherein the metal hydride reducing agent for eliminating the excess or unreacted acetaldehyde is selected from the group consisting of sodium borohydride, amine boranes, lithium aluminum hydride and mixtures thereof.

11. The process of claim 10 wherein the metal hydride reducing agent for eliminating the excess or unreacted acetaldehyde is sodium borohydride.

12. The process of claim 1 wherein an aqueous buffer is added after the excess acetaldehyde has been reduced to maintain the pH in the range of about 7–12.

13. The process of claim 12 wherein the pH is maintained within the range of about 9.5–10 after the addition of the buffer.

14. The process of claim 13 wherein the aqueous buffer is selected from the group consisting of borate, phosphate, citrate buffers and mixtures thereof.

15. The process of claim 14 wherein the buffer is sodium borate.

16. The process of claim 1 wherein the 1-N-ethylidene group is reduced to the ethylamino group by the addition of a reducing agent selected from the group consisting of sodium borohydride, amine boranes, lithium aluminum hydride and mixtures thereof.

17. The process of claim 16 wherein the ethylidene substituent is reduced to the ethylamino substituent by the addition of sodium borohydride.

18. A selectively blocked sisomicin derivative of the formula

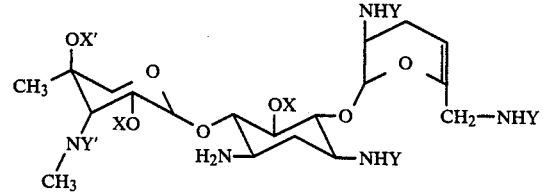

wherein
each X is an organosilyl group

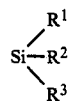

with $R^1$ to $R^3$ independently being lower alkyl, phenyl, or phenylloweralkyl;

X' is hydrogen or an organosilyl group as defined above;

each Y represents an amino blocking group; and,

Y' represents hydrogen or an amino blocking group.

19. The compound of claim 18 wherein each X is trimethylsilyl.

20. The compound of claim 18 wherein each Y is acetyl.

21. The compound of claim 18 above wherein Y' is hydrogen.

22. A selectively blocked sisomicin derivative of the formula

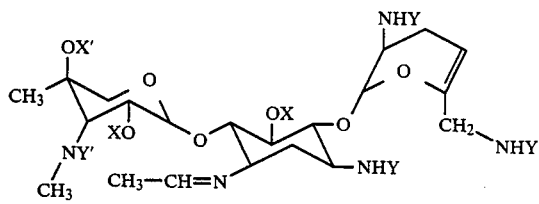

wherein
each X is an organosilyl group

with $R^1$ to $R^3$ independently being lower alkyl, phenyl or phenyllower alkyl;

X' is hydrogen or an organosilyl group as defined above;

each Y represents an amino blocking group; and,

Y' represents hydrogen or an amino blocking group.

23. The compound of claim 22 wherein X is trimethylsilyl.

24. The compound of claim 23 wherein Y is acetyl.

25. The compound of claim 22 wherein X' is trimethylsilyl.

26. The compound of claim 22 above wherein Y' is hydrogen.

27. 3,2',6'-tri-N-acetyl-1-N-ethylidene-5,2'',-4''-trimethylsilylsisomicin.

28. The process of claim 1 wherein the sisomicin derivative as defined in claim 1 is prepared by silyating a sisomicin compound wherein X is hydrogen, X' is hydrogen, Y is acetyl and Y' is hydrogen with a compound selected from the group consisting of hexamethyldisilazane, bis(trimethylsilyl) acetamide, mono(trimethylsilyl) acetamide, trimethylchlorosilane, and mixtures thereof.

29. The method of claim 28 wherein the sisomicin derivative is silylated by contacting the sisomicin comopund with hexamethyldisilazane.

30. The method of claim 29 wherein the silylation is catalyzed by a catalyst selected from the group consisting of a sulfate salt, an ammonium salt, sulfuric acid, trimethyl silylchloride, and mixtures thereof.

31. The method of claim 30 wherein the silylation is conducted in the presence of 3,2',6'-tri-N-acetylsisomicin sulfate.

* * * * *